United States Patent [19]
Kaemmerer

[11] Patent Number: 5,693,076
[45] Date of Patent: Dec. 2, 1997

[54] COMPRESSED PATIENT NARRATIVE STORAGE IN AND FULL TEXT RECONSTRUCTION FROM IMPLANTABLE MEDICAL DEVICES

[75] Inventor: William F. Kaemmerer, Edina, Minn.

[73] Assignee: Medtronic, Inc., Minneapolis, Minn.

[21] Appl. No.: 585,222

[22] Filed: Jan. 16, 1996

[51] Int. Cl.⁶ ............................ A61N 1/362; A61N 1/36
[52] U.S. Cl. ................... 607/59; 607/32; 607/30
[58] Field of Search .................. 607/59, 32, 60, 607/30; 128/903

[56] References Cited

U.S. PATENT DOCUMENTS

| | | | |
|---|---|---|---|
| H1347 | 8/1994 | Greeninger et al. | 607/30 |
| 4,365,290 | 12/1982 | Nelms | 607/16 |
| 4,374,382 | 2/1983 | Markowitz | 607/27 |
| 4,424,812 | 1/1984 | Lesnick | 607/30 |
| 4,726,380 | 2/1988 | Vollmann | 607/15 |
| 4,804,950 | 2/1989 | Moon et al. | 128/710 |
| 4,809,697 | 3/1989 | Causey | 607/30 |
| 5,105,220 | 4/1992 | Knodt | 355/209 |
| 5,127,404 | 7/1992 | Wybomy | 607/32 |
| 5,168,871 | 12/1992 | Grevious | 128/903 |
| 5,224,486 | 7/1993 | Lerman | 128/696 |
| 5,312,446 | 5/1994 | Holschbach | 607/30 |
| 5,330,513 | 7/1994 | Nichols | 607/32 |
| 5,345,362 | 9/1994 | Winkler | 361/681 |
| 5,350,411 | 9/1994 | Ryan | 607/60 |
| 5,372,607 | 12/1994 | Stone | 607/30 |
| 5,444,617 | 8/1995 | Merialdo | 364/419.1 |
| 5,490,061 | 2/1996 | Tolin et al. | 364/419.02 |
| 5,545,186 | 8/1996 | Olson et al. | 607/14 |
| 5,607,460 | 3/1997 | Kroll et al. | 607/59 |

OTHER PUBLICATIONS

Hopcroft, John E. et al., "*Introduction to Automata Theory, Languages, and Computation*", Addison–Wesley Publishing Company, 1979, pp. 77–106.

*Primary Examiner*—William E. Kamm
*Assistant Examiner*—Carl H. Layno
*Attorney, Agent, or Firm*—Reed A. Duthler; Harold R. Patton

[57] ABSTRACT

A system and method of operation thereof for storing patient related data within an implanted medical device and retrieving and regenerating the patient related data using a generative grammar and graphic user-interface software in a programmer having uplink and downlink telemetry capabilities. A generative grammar resident in the programmer is selected, and it prompts a physician or other user to enter patient specific variables by selecting menu choices or making data entries in data entry fields which generated by grammar rules while constructing a textual narrative report about the patient in a human language. Simultaneously, in the programmer, a digital patient related data bit string is assembled that identifies the generative grammar and encodes the choices and values as they are entered by the physician. Also simultaneously, internal computer records of the patient related data are stored in computer memory. The generative grammar invokes text and menus or data entry fields for the continuing narrative that depend upon the preceding narrative in a grammatically correct manner. When the narrative is completed, the simultaneously generated bit string is stored in the implanted medical device using conventional downlink telemetry. The stored bit string may be telemetered out on command and decoded to identify the generative grammar and then to use the generative grammar to regenerate the textual narrative in either the original human language or in an alternative human language for which a corresponding generative grammar exists in the programmer.

24 Claims, 11 Drawing Sheets

History entered: 8 September 1995 by Z----
Mr. Perkins is a 61 year-old male with primary VF arrest and recurrent syncopal VT secondary to coronary artery disease (CAD).

He underwent a CABG on 5 December 1989 and a CABG re-do on 5 October 1994. His LV ejection fraction was 45% as measured by cardiac catheterization on 5 October 1994.

October 1994 behandelt.

FIG. 8

File Edit

Electronic Chart Notes—Medtronic confidential    Thu 2:21 PM

Dictate:

Patient (last name): Perkins

Birthdate: 1/2/34

● male  ○ female

| Parameter Change History | Cardiac History |

Pacing Threshold Trend | Medications Narrative | Latest FU:Dec.18,199

Lead Impedance Trend | Adverse drug reactions | EGM samples:NSR, VT

Implant Values—DFT etc. | Medications–discontinued | Arrhythmia Therapy History

Medications–current

Integrated Time-Line

Uplinked medication records:

* Dr. B----- started Mr. Perkins on Digoxin on 5 December 1989 at a dosage of 0.20 mg per day to treat symptoms of heart failure.

* Dr. B----- changed the dosage for Mr. Perkins's Digoxin from 0.20 mg per day to 0.10 mg per day on 15 February 1990 to adjust to a maintenance dosage.

* Dr. B----- discontinued Mr. Perkins's Digoxin on 1 December 1995 because of diminished renal function and replaced it with Mexiletine at a dosage of 300 mg q8h to treat sustained VT.

Dictation Controls:
[Start]
[Cancel]
[Start Over]
[Backspace]

Demo
clear:
[Prg] [PCD]
[ENGLISH ▶]
[Perkins ▶]

[uplink] 618
[down]   0

0001010000000000Y---"B----"Z----""Perkins"10000011110001011OZ-----"0110011100010111000000000

COMPRESSED PATIENT NARRATIVE STORAGE IN AND FULL TEXT RECONSTRUCTION FROM IMPLANTABLE MEDICAL DEVICES

FIELD OF THE INVENTION

The present invention relates to a system for storing patient data in an implanted medical device and retrieving and reconstituting the patient data from the medical device through the use of a device programmer, and more particularly to such a system allowing the patient dam to be entered by the physician as narrative text in a human language following a formal generative grammar, stored in minimal memory in the medical device, and retrieved on command from the medical device and reconstructed in narrative text or summary text in the same or another selected human language.

BACKGROUND OF THE INVENTION

Over the years, many implantable medical devices have been developed for monitoring a medical condition and/or providing a therapy to a patient. Such devices include electrical stimulation devices for stimulating body organs and tissue to evoke a response for enhancing a body function or to control pain and drug delivery devices for releasing a drug bolus at a selected site. Other more passive medical devices have been developed for simply monitoring a patient's condition.

Chronically implanted cardiovascular devices for monitoring cardiovascular conditions and providing therapies for treating cardiac arrhythmias have vastly improved patient's quality of life as well as reduced mortality in patient's susceptible to sudden death due to intractable, life threatening tachyarrhythmias. As implanted device technology has grown more sophisticated with capabilities to diagnose and treat a greater range of patient conditions, including otherwise life threatening conditions, patients are allowed the freedom from hospital or home confinement or bed rest. The resulting improved patient mobility is a principal rationale for such devices. However, the improved mobility brings with it the need to maintain the ability to communicate with the implanted device for a variety of reasons.

Early in the development of cardiac pacemakers, patient follow-up to monitor pacemaker operation was facilitated by telephonic transmissions of skin surface ECGs in real time to a physician's office employing such systems as the MEDTRONIC® TeleTrace® ECG transmitter. Over time, various patient worn, ambulatory ECG and device monitors have been developed for providing ECG data for analysis of cardiac arrhythmias. At the same time, implantable medical devices were designed to be programmable in operating mode and parameters employing "telemetry" transceivers in the implanted medical device and an external programmer.

In the case of current technology arrhythmia control devices, e.g. multiprogrammable, cardiac pacemakers and pacemaker-cardioverter-defibrillators, a relatively wide range of device operating modes and parameters are remotely programmable to condition the device to diagnose one or more cardiac arrhythmias and deliver an appropriate therapy. In cardiac pacemakers, the pacing rate in one or both heart chambers is governed by algorithms that process the underlying cardiac rhythm as well as physiologic conditions, e.g. patient activity level and other measured variables, to arrive at a suitable pacing rate. The pacemaker operating modes and the algorithm for establishing the appropriate pacing rate are programmed into internal memory by accessing the implanted pacemaker's telemetry transceiver with an external programmer during a downlink telemetry transmission. Similarly, with pacemaker-cardioverter-defibrillator devices, the diagnosis of a tachyarrhythmia requiring delivery of a treatment therapy and the therapies to be delivered are governed by operating modes and algorithm parameters that may be programmed into device memory using such a programmer.

Moreover, such implanted devices have the capability to process the patient's electrogram and any measured physiological conditions employed in the diagnosis and to store the data, particularly such data that is related to a detected arrhythmic episode satisfying the criteria for treatment, for subsequent telemetry out or uplink telemetry on interrogation of the device memory by the external programmer. The telemetered out data is analyzed and may be employed to establish or refine the operating modes and parameters of the device operating algorithms by re-programming in the corresponding operating mode or parameter data.

A wide variety of programming and interrogation techniques have been devised over the years. Initially, when programming techniques were first devised, the paramount concern addressed related to patient safety. Safeguards were built in to address the concern that the patient could be put at risk of inadvertent mis-programming of the implanted device, e.g. programming too high a rate for a pacemaker or programming the pacing or sensing functions off, by stray electromagnetic fields. For this reason, and in order to avoid high current consumption that would shorten the implanted device fife, telemetry operating range was extremely limited. In systems continuing to the present time, downlink telemetry has required application of a magnetic field at the patient's skin over the implanted device to close a reed switch while RF programming or interrogating commands are generated to be received by the implanted device transceiver. The programming or interrogating commands are decoded and stored in memory or used to trigger uplink telemetry of stored data and operating modes and parameters by the implanted device transceiver.

Examples of such medical device programmers include the Medtronic® Model 9760 pacemaker programmer and the Model 9790 universal programmer for bradycardia pacemakers and tachyarrhythmia devices described in U.S. Pat. Nos. 5,372,607, 5,345,362, and 5,350,411 and variations thereof disclosed in U.S. Pat. No. 5,549,654, incorporated herein by reference in their entireties. Other, earlier medical device programmers are disclosed, for example, in U.S. Pat. Nos. 4,365,290, 4,424,812, 4,726,380 and 4,809,697.

As mentioned above, one of the rationales and attributes of implanted medical devices of the type described is that the patient is allowed to be ambulatory while his/her medical condition is monitored and/or treated by the implanted medical device. As a safety precaution, programmers capable of programming all the operating modes or functions of the implanted device and for initiating interrogation through the telemetry system are generally not provided to the patients. Patients are periodically examined and device interrogation is conducted by the physician using the external programmer during scheduled follow-up visits to the physicians office or clinic. This limits the frequency of monitoring and may require certain patients to remain within easy reach of the physician's office in case of an emergency.

Such emergency conditions, e.g. device failure to deliver a therapy when required, physiologic variable changes resulting in inability of the device to effectively treat the patient, accidents unrelated to the patient's condition being treated, other illnesses or transient problems, etc., may arise unexpectedly and cause a patient to require treatment by a physician unfamiliar with the implanted device or the patient's medical history. Perhaps, for this reason or simply for convenience, it has been proposed in the above-referenced '380 patent to store patient data (listed in Table V thereof) in memory in the implanted medical device that can be interrogated and retrieved by telemetry using a compatible programmer. The '380 patent also describes other types of stored data and the storage of operating and control algorithms in bytes in RAM. A comprehensive listing of data stored in memory in a rate-responsive cardiac pacemaker also appears in U.S. Pat. No. 5,330,513 also incorporated herein by reference in its entirety.

Patients traveling domestically or in a foreign country typically do not carry their medical records with them, although they are instructed to carry identification of the implanted medical device and any medications they are taking. Patients are also typically not fully cognizant of their medical records or able to recite past treatments that may or may not have been effective, medications they are allergic to, and the like. If an emergency arises, and the cause and treatment is not apparent to the medical personnel consulted, then it may be necessary to consult with the patient's primary care physician and await receipt of the patient's medical records before effective treatment can be commenced. Thus, it would be useful to store patient data in the medical device implanted in the patient for retrieval under either routine follow-up or under emergency conditions.

Despite the general desire to do so, the storage of patient data in the limited memory available in such implanted medical devices has not been pursued to any extent because it can consume too many memory bytes that otherwise are considered to be better used to store diagnostic history data and device therapy delivery history data accumulated and stored by the medical device over time as described in the '513 patent and in the above-referenced '607 patent. With increasing memory capacities, future implantable medical devices could also store patient data. However, the straight-forward approach of storing ASCII text in the medical device is an unacceptable strategy. It would be too tedious for the physician to type in patient histories and too time-consuming to telemeter the full text out.

SUMMARY OF THE INVENTION

It is therefore an object of the present invention to provide a system for storing patient medical histories in implantable medical devices that allows for fast and efficient data entry, permits a wide range of expression regarding what the physician says about the patient's condition, and provides for efficient use of telemetry bandwidth and device memory capacity.

It is a further object of the present invention to provide such a system for telemetering out the stored medical histories and displaying the medical histories in text or tabular formats in a selectable human language that is the same or different than the human language used in storing the medical histories.

It is a still further object of the present invention to provide such a system employing a formal regenerative grammar.

These and other objects of the invention are realized in a system and a method for storing patient related data within an implanted medical device implanted in an ambulatory patient and for regenerating the patient related information with an external programmer of the type comprising: an implanted medical device telemetry transceiver in the implanted medical device operable in a downlink telemetry mode for receiving patient related data bit strings and operable in an uplink telemetry mode for transmitting patient related data bit strings; and memory locations in the implanted medical device for storing patient related data bit strings transmitted in downlink telemetry to the implanted medical device telemetry transceiver; the system and method of encoding and storing textual narrative patient related data in such memory locations employing such an external programmer capable of initiating the uplink and downlink telemetry comprising the means for and steps of: storing, in the external programmer memory, a formal generative grammar defining a finite set of variables and text governed by a set of grammar rules from which a textual narrative of patient related data can be generated by appropriate selections of choices from menus and values of variables; encoding selections of choices from menus and values of variables as a patient related data bit string; and operating the programmer telemetry transceiver in the downlink telemetry mode for signaling the implanted medical device telemetry transceiver to operate in the downlink telemetry mode and for transmitting the patient related data bit string to the implanted medical device telemetry transceiver for receipt and storage in the implanted medical device memory locations.

The method and system preferably further comprises the step of and means for appending an identification code of the grammar with the patient related data bit string. The method and system also preferably further comprises the steps of and means for: operating the programmer telemetry transceiver in the uplink telemetry mode for signaling the implanted medical device telemetry transceiver to operate in the uplink telemetry mode and for transmitting the patient related data bit string to the programmer telemetry transceiver for receipt thereby; identifying the formal generative grammar from the identification code; and regenerating the textual narrative patient related data from the identified generative grammar and the patient related data bit string. The regenerating may also include presenting selected patient data from the patient related data bit string in tabular format.

In addition, the regenerating step and means further comprise regenerating the textual narrative patient related data from the patient related data bit string in any selected human language for which there exists a formal generative grammar that is correlated to the original formal generative grammar used to enter and store the patient related data.

In the practice of the invention, a generative grammar resident in the programmer is selected, and by following that generative grammar, a software algorithm in the programmer prompts a physician to enter information by selecting menu choices or making data entries in data entry fields. These choices and values are used within the framework of the grammar rules comprising the grammar to construct a textual narrative about a patient in a human language. In the programmer, a digital bit string is assembled that identifies the generative grammar and encodes the choices and values as they are entered by the physician into a patient related data bit string. Simultaneously, the corresponding textual narrative is composed and displayed for the physician, and an internal computer record of patient related data is maintained. The physician's entries invoke text and menus or data entry fields for the continuing narrative that depend upon the preceding narrative in a grammatically correct manner. When the narrative is completed, the resulting patient related data bit string is stored in the implanted medical device using conventional downlink telemetry. The stored patient related data bit string may be telemetered out on command and decoded to identify the generative grammar and to then regenerate the textual narrative or to assemble tabular data or the like in either the original human language or in any selected human language for which a corresponding generative grammar exists. The regenerating process involves using the programmer-resident generative grammar to reconstruct the narrative and display it in the human language of the programmer-resident grammar in textual narrative form and to extract defined data for display in alternative tabular form.

Advantageously, the patient related bit string, because it typically is an order of magnitude more compact than the narrative text it encodes, may be efficiently telemetered into a minimal amount of memory of an implanted medical device. Storage of only the patient name, patient specific variables, including menu choices and alphanumeric data, allows paragraphs of regenerable text (several kilobytes in size) to be telemetered and stored in the device as several hundred bits. Only the comprehensiveness of the generative grammar, and not the amount of memory in the medical device nor the software in the programmer, determines what can be expressed by the physician about the patient, encoded as a bit string and stored in the implanted medical device.

It is therefore possible to provide physicians with a means of composing and storing textual information about a patient's medical history, medications, rationale for treatment, etc., in his/her implanted medical device without requiting extensive typing or lengthy telemetry times. This information is then available to any physician with access to a programmer with the appropriate programmer-resident generative grammars, whenever the device memory is interrogated, regardless of where the patient travels. The generative grammar-based approach to patient data storage as described above is independent of the architecture, telemetry speed, and memory format of the implanted medical device.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

FIG. 6 is an illustration of one screen in the entry of a narrative of patient related data related to the cardiac history of the patient, showing the selection of choices from menus specified by the formal generative grammar;

FIG. 7 is an illustration of one screen in the entry of a narrative of patient related data showing the completed textual narrative for the cardiac history of the patient;

FIG. 8 is an illustration of one screen in the retrieval of the patient related data bit string and regeneration of a narrative of patient related data, using a correlated formal generative grammar in the German language, showing the resulting German language form of the completed textual narrative for the cardiac history of the patient;

FIG. 9 is an illustration of one screen in the retrieval of patient related data regarding the medications prescribed by physicians for the patient, showing the textual narratives reconstructed from the patient related bit string using the programmer-resident generative grammar;

FIG. 10 is an illustration of a further addition made to the patient related data regarding the medications prescribed by the physician, using menu choices specified by the generative grammar;

FIG. 11 is an illustration of a tabular format report regarding the patient's current medications extracted from the patient related data bit string and displayed in alternative tabular form.

DETAILED DESCRIPTION OF THE PREFERRED EMBODIMENTS

The present invention can readily be practiced using the basic hardware and software of such existing microprocessor-controlled, multi-programmable, implantable pacemakers, pacemaker-cardioverter-defibrillators, and other medical devices, having uplink and downlink telemetry capabilities with an external, microprocessor-based programmer of the types described above with reference to FIGS. 1–4. The system shown in FIGS. 1–4 includes a pacemaker 10, for example, which has been implanted in a patient 12. It also shows an external programmer 20.

Figure 1:
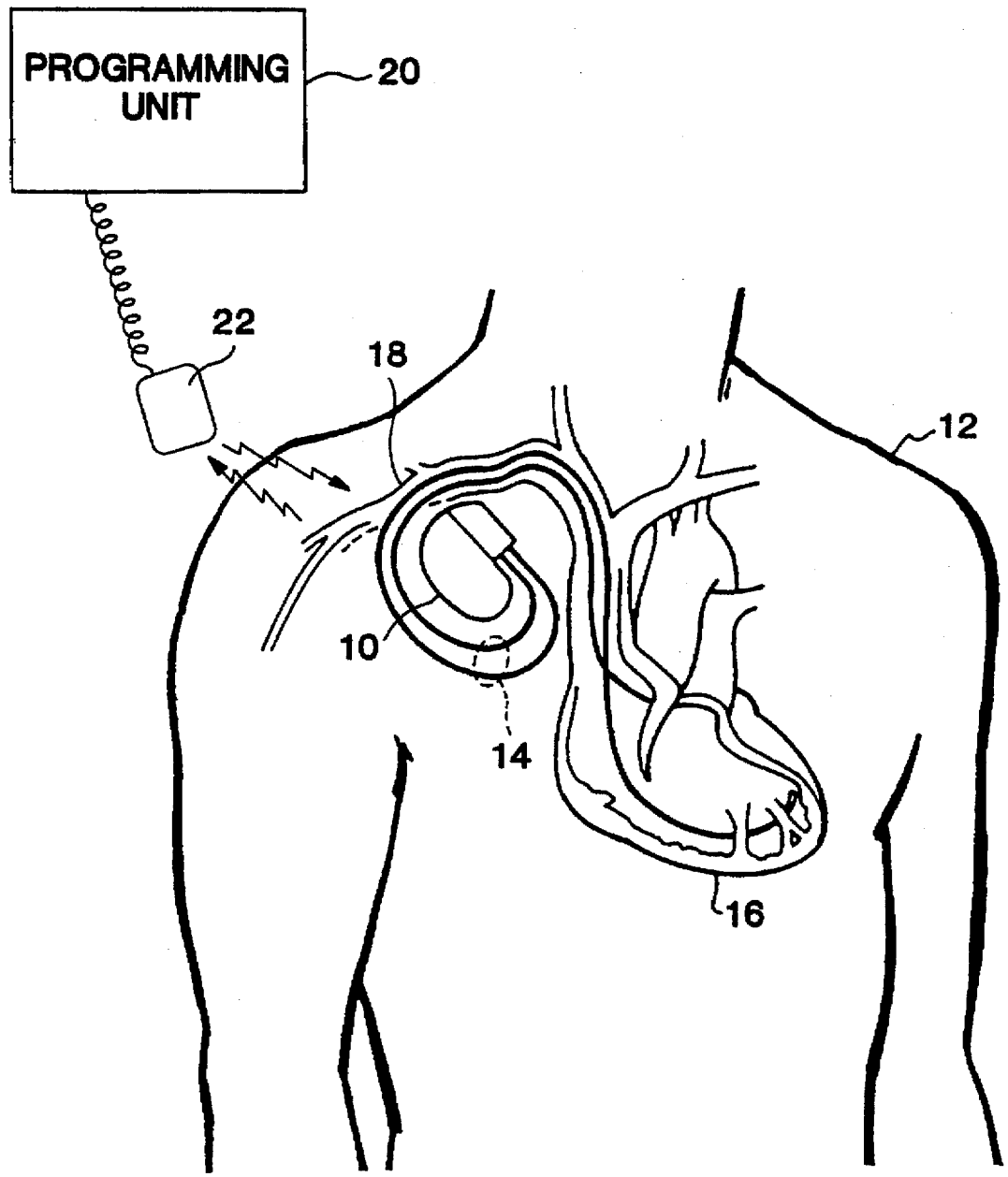
FIG. 1 is a simplified view of an implanted medical device in a patient and an external programmer for providing uplink and downlink telemetry with the implanted device in which the present invention may be implemented.

In accordance with conventional practice in the art, pacemaker 10 is housed within a hermetically sealed, biologically inert outer canister, which may itself be conductive so as to serve an indifferent electrode in the pacemaker's pacing/sensing circuits. One or more pacemaker leads, collectively identified with reference numeral 14 in FIG. 1, are electrically coupled to pacemaker 10 in a conventional manner and extend into the patient's heart 16 via a vein 18. Disposed generally near the distal end of leads 14 are one or more exposed conductive electrodes for receiving electric cardiac signals and/or for delivering electrical pacing pulses to heart 16. As will be appreciated by those of ordinary skill in the art, leads 14 may be implanted with its distal end situated in either the atrium or ventricle of heart 16.

The external programmer 20 is provided for non-invasive communication with implanted pacemaker 10 via uplink and downlink telemetry hereinafter described in further detail. Associated with programmer 20 is a programming head 22 for facilitating telemetric communication between implanted pacemaker 10 and programmer 20. The programming head 22 is positioned on the patient's body over the implant site of the pacemaker 10, such that one or more antennas within the head 22 can send pulse modulated RF signals to, and receive pulse modulated RF signals from, an antenna disposed within the hermetic enclosure of the implanted pacemaker 10 in accordance with common practice in the art.

Figure 2:
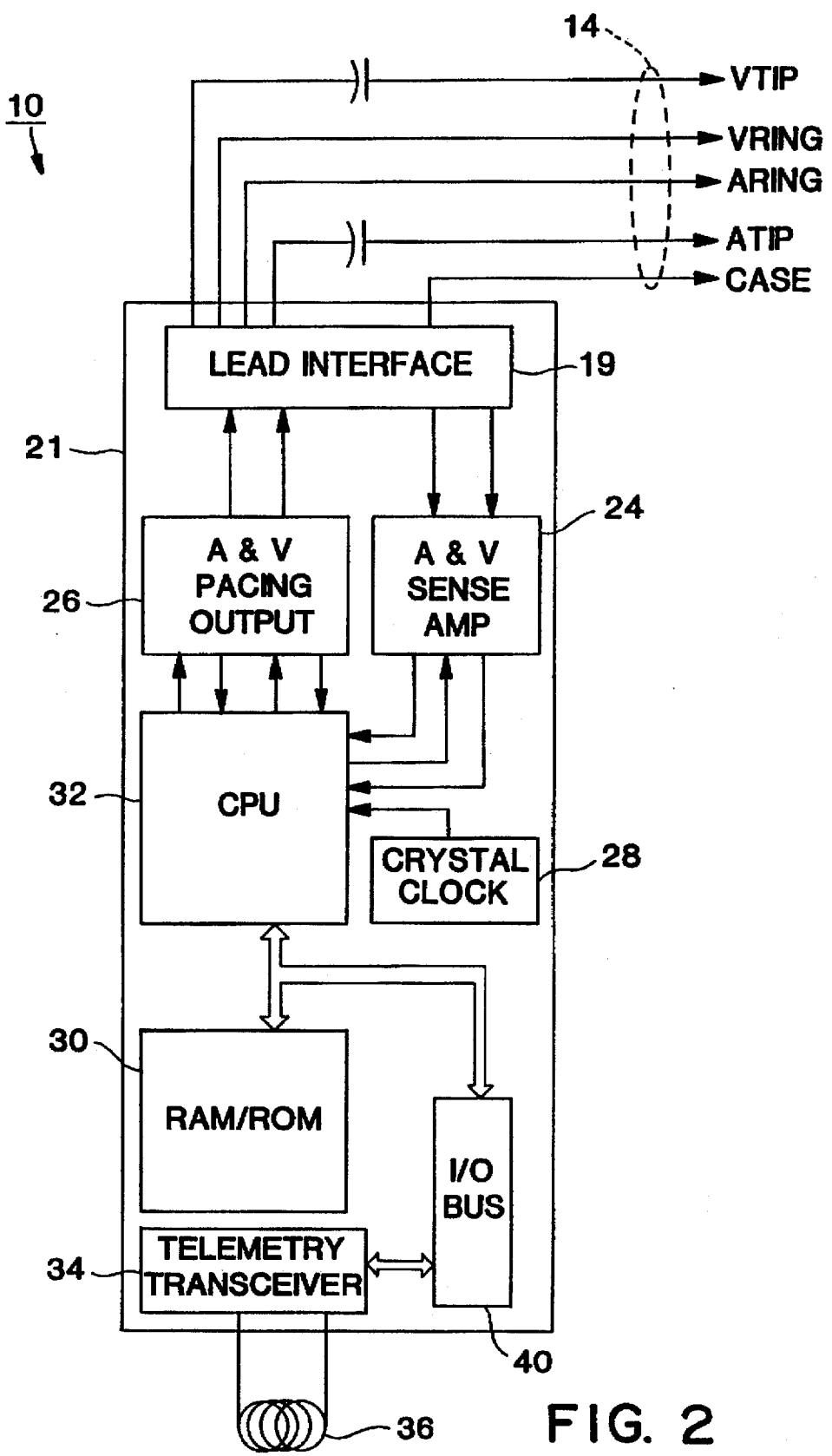
FIG. 2 is a simplified block diagram of the major components of the implanted medical device of FIG. 1.

Turning now to FIG. 2, it depicts a block diagram of the major components of pacemaker 10 including a primary control circuit 21 for controlling the device's pacing, sensing and data telemetry functions. Control circuit 21 in FIG. 2 includes sense amplifier circuit 24, stimulating pulse output circuit 26, a crystal oscillator clock 28, a random-access memory and read-only memory (RAM/ROM) unit 30, central processing unit (CPU) 32, internal telemetry transceiver 34, and I/O bus 40 all of which are well-known in the art. A lead interface 19 is provided for coupling the atrial and ventricular pacing output circuits 26 and sense amplifier circuits 24 to the atrial and ventricular leads 14 described in reference to FIG. 1 in a manner also well known in the art. The specific connections between the circuit blocks and the lead interface 19 and I/O interface 40 are also simplified in FIG. 2. Control circuit 21 may be of conventional design in accordance with any of the above-referenced patents disclosing pacemakers and represents a simplification of the pacemaker circuits disclosed therein, e.g. FIG. 1 of the '411 patent, for example.

As previously noted, control circuit 21 includes CPU 32 which may be an off-the-shelf programmable microprocessor or microcontroller, but in the presently preferred embodiment of the invention is a custom integrated circuit. Although specific connections between CPU 32 and the other components of control circuit 21 are simplified in FIG. 2, it will be apparent to those of ordinary skill in the art that CPU 32 functions to control the timed operation of stimulating pulse output circuit 26 and sense amplifier circuit 24 under control of algorithms stored in RAM/ROM unit 30 and operating modes and parameters that are programmed in and stored in RAM/ROM unit 30.

It is to be understood that the various components of pulse generator 10 depicted in FIG. 2 are powered by means of a battery (not shown) which is contained within the hermetic enclosure of pacemaker 10, in accordance with common practice in the art. For the sake of clarity in the Figures, the battery and the connections between it and the other components of pulse generator 10 are not shown.

The telemetry transceiver 34 is coupled to the telemetry antenna 36 and is operated under the control of CPU 32 in a downlink telemetry mode for receiving, decoding and storing programmed-in commands and dam in RAM/ROM unit 30 and in an uplink telemetry mode for encoding and transmitting out stored data and certain digitized real time data in a manner well known in the art. For example, the telemetry system described in the above-referenced '411 patent and in U.S. Pat. No. 5,127,404, incorporated herein by reference in its entirety, set forth suitable pulse modulation encoding and decoding regimens for the data bits encoded within the RF telemetry signals. The present invention does not modify the telemetry system in any way, and hence reference is made to the incorporated disclosures of these patents.

Figure 3:
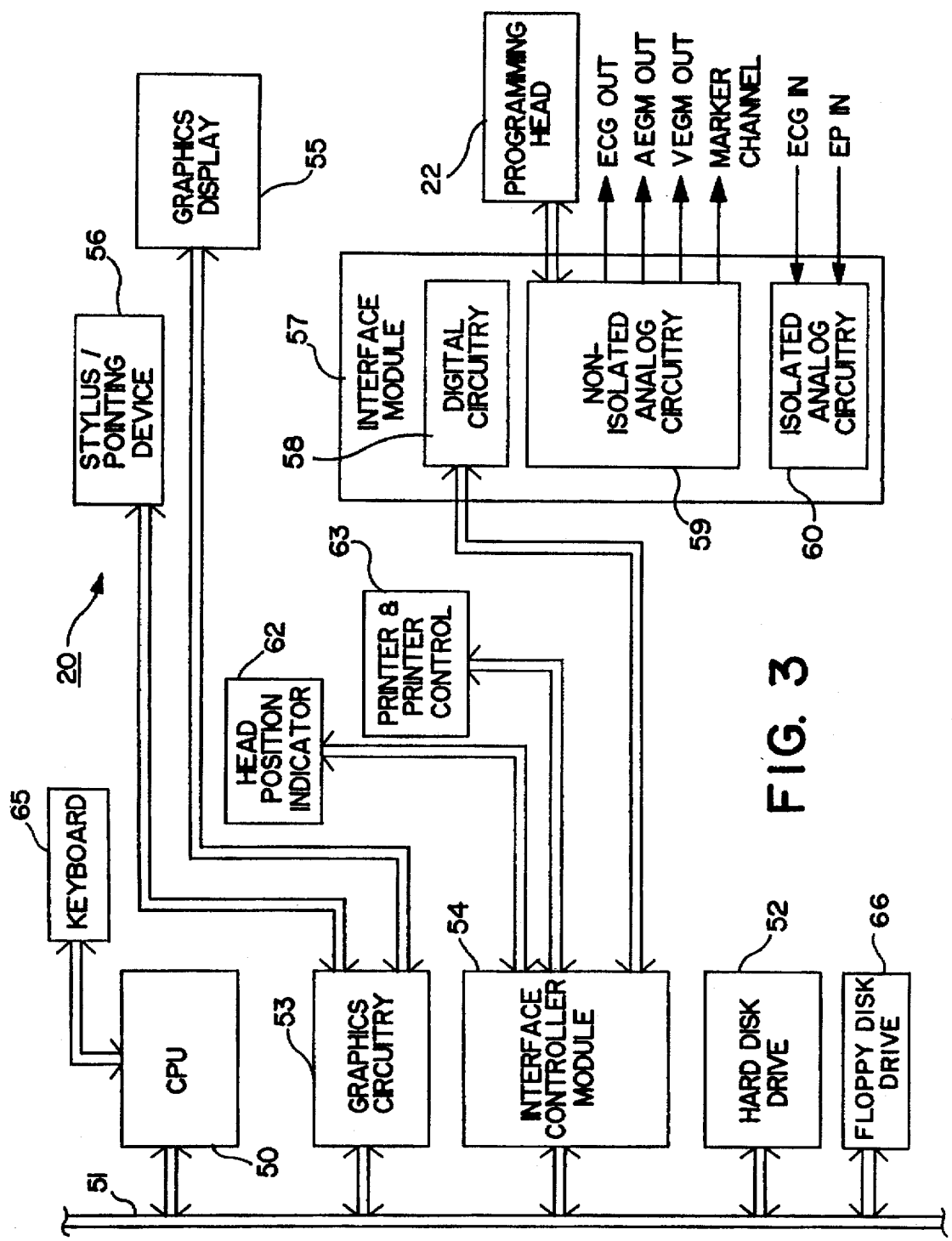
FIG. 3 is a simplified block diagram of the major components of the external programmer of FIG. 1.

A generalized block diagram of programmer 20, which is preferably the above-referenced Medtronic® Model 9760 or 9790 programmer and depicted in detail in the above-incorporated '362 patent, is set forth in FIG. 3. As shown in FIG. 3, programmer 20 is a personal computer type, microprocessor-based device incorporating a central processing unit 50, which may be, for example, an Intel 80386 or 80486 or Pentium microprocessor or the like. A system bus 51 interconnects CPU 50 with a hard disk drive 52 storing operational programs and data and with a graphics circuit 53 and an interface controller module 54. A floppy disk drive 66 (or a CD ROM drive 70 shown in FIG. 4) is also coupled to bus 51 and is accessible via a disk insertion slot (shown as slot 68 in FIG. 4) within the housing of the programmer 20. Programmer 20 further comprises an interface module 57 which includes digital circuit 58, non-isolated analog circuit 59, and isolated analog circuit 60. Digital circuit 58 enables interface module 57 to communicate with interface controller module 54.

In order for the physician or other care giver or user to communicate with the programmer 20, a keyboard 65 coupled to CPU 50 is optionally provided. However the primary communication mode is through graphics display screen 55 of the well-known "touch sensitive" type controlled by graphics circuit 53. A user of programmer 20 may interact therewith through the use of a stylus 56, also coupled to graphics circuit 53, which is used to point to various locations on screen 55 which display menu choices for selection by the user or an alphanumeric keyboard for entering text or numbers and other symbols as shown in the above-incorporated '362 patent. Various touch-screen assemblies are known and commercially available. Graphics display screen 55 is used to display the patient related data and menu choices and data entry fields used in entering the data in accordance with the present invention as described below.

Graphics display 55 also displays a variety of screens of telemetered out data or real time data. Programmer 20 is also provided with a strip chart printer 63 or the like coupled to interface controller module 54 so that a hard copy of a patient's ECG, EGM, marker channel or of graphics displayed on the display 55 can be generated.

As will be appreciated by those of ordinary skill in the art, it is often desirable to provide a means for programmer 20 to adapt its mode of operation depending upon the type or generation of implanted medical device to be programmed. Accordingly, it may be desirable to have an expansion cartridge containing EPROMs or the like for storing software programs to control programmer 20 to operate in a particular manner corresponding to a given type or generation of implantable medical device. In addition, in accordance with the present invention, it is desirable to provide the capability through the expansion cartridge or through the floppy disk drive 66 or the CD ROM drive 68 (shown in FIG. 4) to expand or alter the formal generative grammars stored therein or in hard disk drive 52 as experience dictates the need or opportunity to do so.

The non-isolated analog circuit 59 of interface module 57 is coupled to a programming head 22 which is used to establish the uplink and downlink telemetry links between the pacemaker 10 and programmer 20 as described above. The atrial and ventricular sense amp circuits 24 of pacemaker 10 of FIG. 2 may also be provided with (electrogram) EGM amplifiers which produce atrial and ventricular EGM signals. These A EGM and V EGM signals may be digitized and uplink telemetered to programmer 20 on receipt of a suitable interrogation command. The uplink telemetered EGM signals are received in programming head 22 and provided to non-isolated analog circuit 59. Non-isolated analog circuit 59, in turn, converts the digitized EGM signals to analog EGM signals (as with a digital-to-analog converter, for example) and presents these signals on output lines designated in FIG. 3 as A EGM OUT and V EGM OUT. These output lines may then be applied to a strip-chart recorder 63 to provide a hard-copy printout of the A EGM or V EGM signals transmitted from pacemaker 10 for viewing by the physician. As these signals are ultimately derived from the intracardiac electrodes, they often provide different information that may not be available in conventional surface ECG signals derived from skin electrodes.

Pacemaker 10 may also be capable of generating so-called marker codes indicative of different cardiac events that it detects. A pacemaker with marker-channel capability is described, for example, in U.S. Pat. No. 4,374,382 to Markowitz, which patent is hereby incorporated by reference herein in its entirety. The markers provided by pacemaker 10 may be received by programming head 22 and presented on the MARKER CHANNEL output line from non-isolated analog circuit 59.

Isolated analog circuit 60 in interface module 57 is provided to receive external ECG and electrophysiologic (EP) stimulation pulse signals. In particular, analog circuit 60 receives ECG signals from patient skin electrodes and processes these signals before providing them to the remainder of the programmer system in a manner well known in the art. Circuit 60 further operates to receive the EP stimulation pulses from an external EP stimulator for the purposes of non-invasive EP studies, as is also known in the art.

In order to ensure proper positioning of programming head 22 over the antenna 36 of pacemaker 10, feedback is provided to the physician that the programming head 22 is in satisfactory communication with and is receiving sufficiently strong RF signals from antenna 36 of pacemaker 10. This feedback may be provided, for example, by means of a head position indicator, e.g. a light-emitting diode (LED) or the like that is lighted to indicate a stable telemetry channel.

The present invention is embodied in software resident in hard disk drive 52 (or any other data storage medium), for example, for encoding narrative information about a patient in compact, bit string form prior to transmitting it via downlink telemetry, and subsequently decoding the uplink telemetered bit string into grammatically correct text and internal computer records 104 of patient data values in RAM 30, from which textual narrative or tabular format reports may be displayed on graphics display 55.

Figure 4:
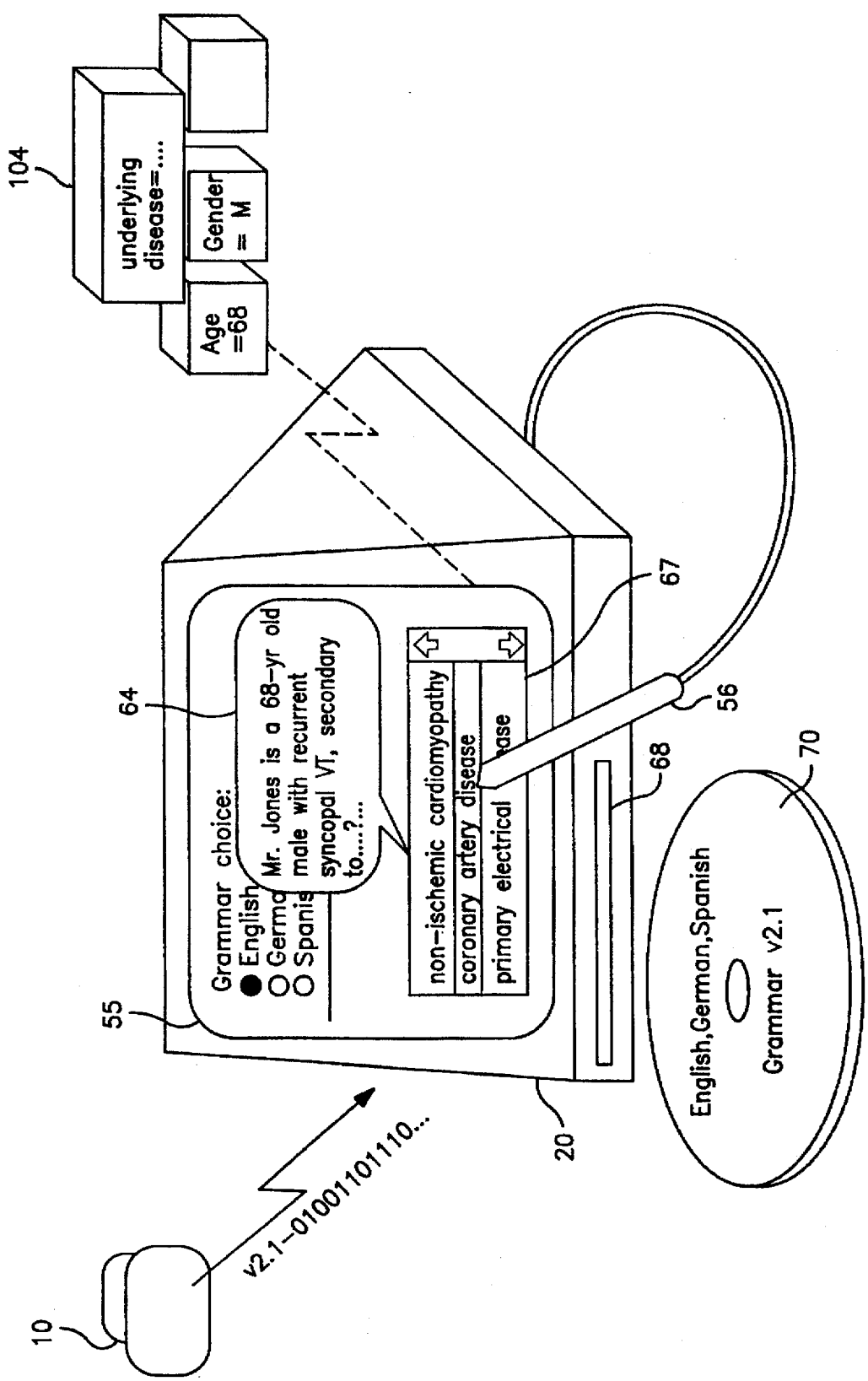
FIG. 4 is a schematic illustration of the system of the present invention for storing patient medical records in memory in an implanted medical device of the type shown in FIGS. 1 and 2.

The data entry and encoding process is depicted in FIG. 4. The data entry and encoding process uses software to: (a) prompt a physician for information used to construct a narrative report 64 about a patient, using a formal generative grammar read from a disk storage device such as CD ROM 70; (b) simultaneously construct a string of bits encoding the choices made by the physician in writing the narrative; and (c) simultaneously build an internal computer representation 104 of the patient's medical record. The physician makes selections from menus (such as the menu 67) using the stylus/pointing device 56 and the graphic display 55. The internal computer representation 104 allows menu choices (such as the menu 67) for further portions of the narrative 64 to reflect what has been described about the patient so far in this same narrative. The resulting patient related data bit string, because it typically is an order of magnitude more compact than the narrative text it encodes, may be efficiently telemetered into the memory of an implanted medical device 10.

Figure 5:
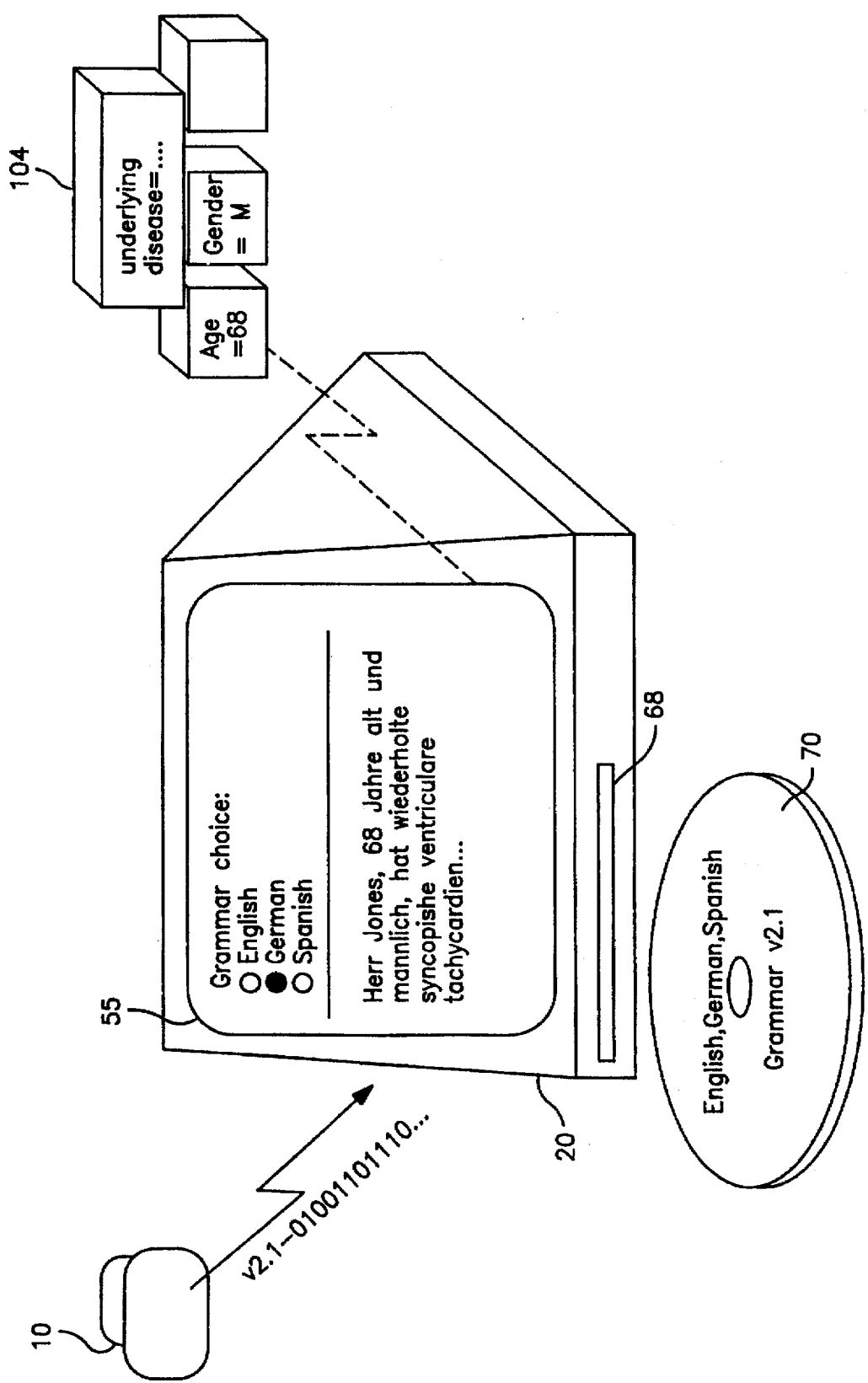
FIG. 5 is a further schematic illustration of the system of the present invention showing the retrieval of patient medical records from memory in an implanted medical device, and regeneration of the narrative in an alternative human language using a corresponding formal generative grammar.

The decoding process is depicted in FIG. 5. The decoding process involves first retrieving the identical bit string from the implanted device 10 by uplink telemetry. Then, the decoding process uses software to: (a) reconstruct the narrative as entered by the physician, by interpreting the bits as representing choices made at choice points in the formal generative grammar used to originally enter the narrative; and (b) simultaneously build an internal computer model 104 of the patient's medical record using the information in the narrative. The output displayed to the physician can be either the original narrative text in the human language in which it was entered, or an equivalent narrative in an alternative human language generated by following a correlated generative grammar, in the alternative human language, using the same patient related data bit string.

The only requirement for two generative grammars in two different human languages to be correlated, and thus meaningfully accept the same patient related data bit string as input, is that the overall menu structure presented to the physician as a result of following one generative grammar must be the same as will arise when following the other generative grammar and making the same data entries. This overall menu structure is determined by the collection of grammar rules comprising a generative grammar, and not by the specific textual words nor the order of words within an individual generative grammar rule. Consequently, by having a human who is fluent in two human languages translate the generative grammar rules from one human language into a second human language one rule at a time, a second, correlated generative grammar in the second human language is created. Regenerating the textual narrative of the patient's data in the second human language is then accomplished by having the programmer-resident software algorithm apply the second, correlated generative grammar, rather than the first, but using the same patient related data bit string as the source of menu choices and data values as they are encountered while following the generative grammar. The result is that the textual narrative is produced in the second human language, rather than the first.

Figure 6:
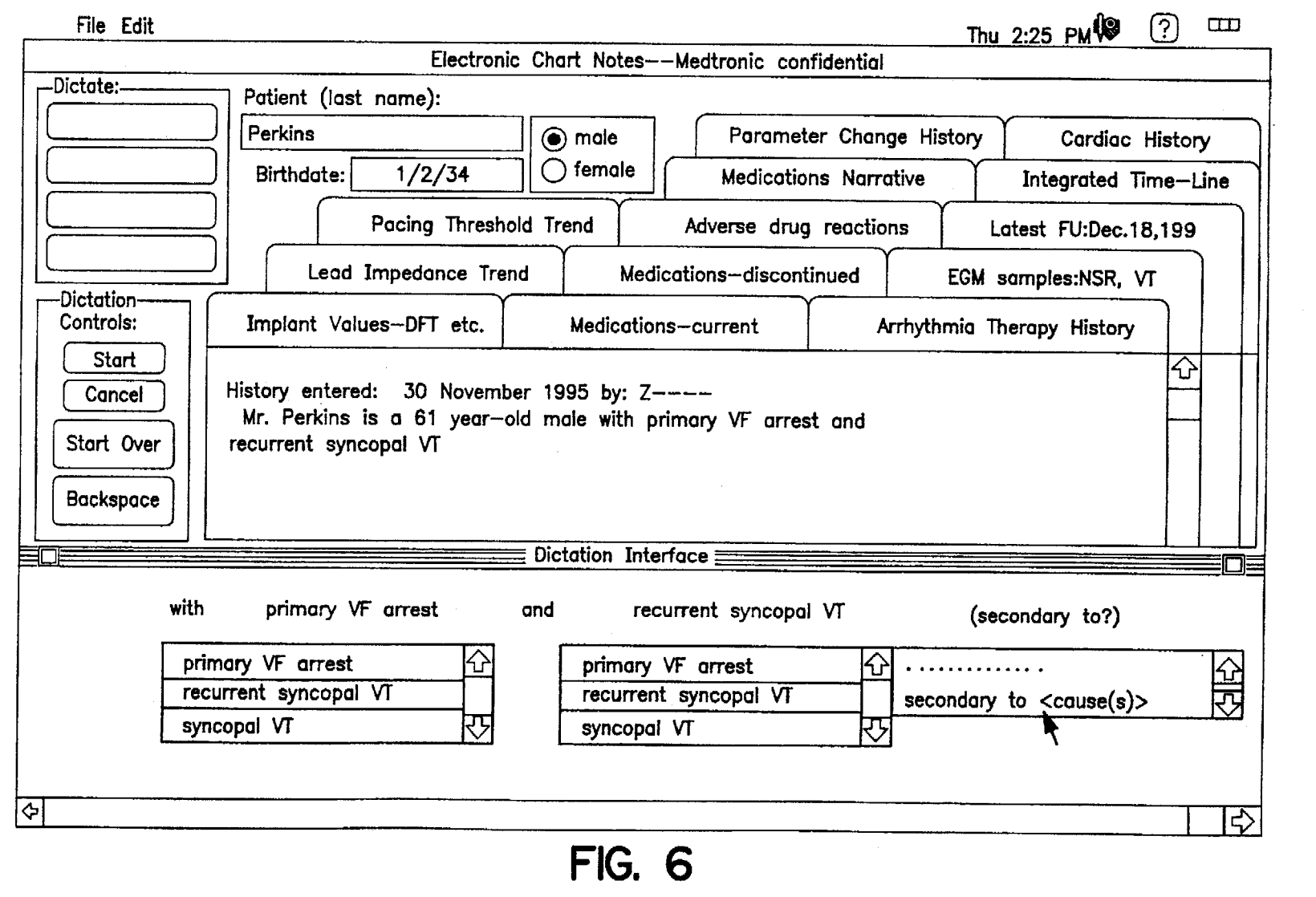

Further details of the data entry process as it may be viewed on the graphics display 55 are shown in FIG. 6 which shows, in progress, the entry of a textual narrative regarding the patient's cardiac history. The bottom portion of the display shows the menus 67 of choices from which the physician is making selections to construct the textual narrative 64 regarding the patient's cardiac history. The arrow in the FIG. 6 represents the stylus/pointing device 56.

FIG. 7 shows the results of the data entry process upon its completion by the physician. The middle portion of FIG. 7 shows the completed textual narrative 64 regarding the patient's cardiac history. The row of ASCII characters "0" and "1" and ASCII characters of physicians' names depict (in human readable form) the patient related data bit string [ref #?] which in binary form is suitable for downlink telemetry to, and uplink telemetry from, the implantable medical device 10. In the portrayed example, the textual narrative shown in FIG. 7 may be encoded into and decoded from a bit suing of 618 bits in length.

Figure 8:
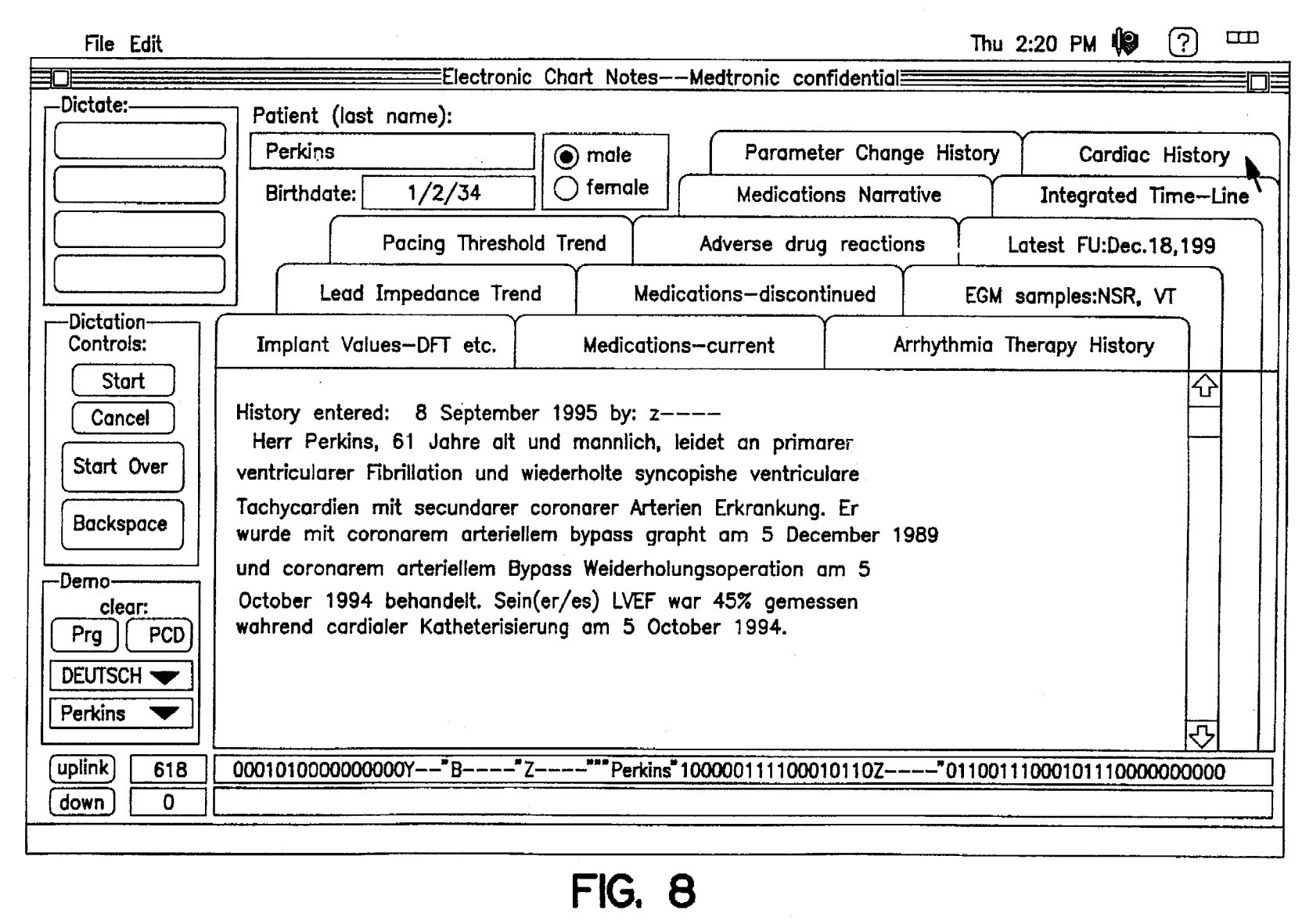

FIG. 8 portrays the result of using the same patient related data bit string shown in textual form in FIG. 7 as input to a corresponding formal generative grammar as may be read from hard disk drive 52 and used by software executed by CPU 50 to generate a corresponding narrative text in an alternative human language, such as German.

FIG. 9 depicts additional portions of the patient related data bit siring, decoded into narrative text form regarding the medications historically prescribed for the patient. The same information decoded from the patient related data bit string into these narratives is also decoded into an internal computer representation 104 from which a tabular format report may be generated by conventional software means well known to those practiced in the art.

Figure 10:
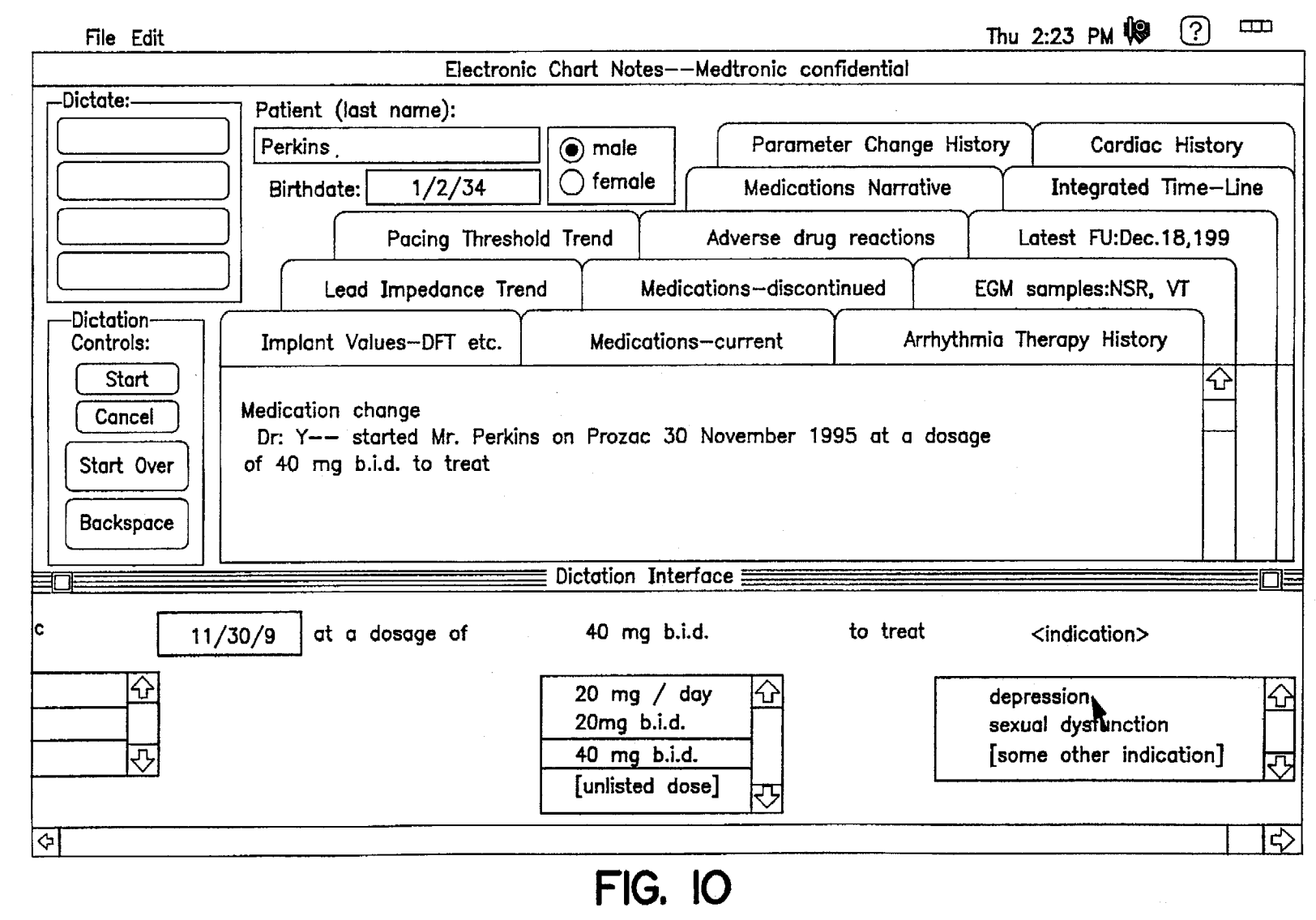

FIG. 10 shows, in progress, the entry of an additional portion of the textual narrative regarding the patient's medication history. The bottom portion of the display shows the menus 67 of choices from which the physician is making selections to construct the textual narrative 64 regarding the actions being taken by the physician with respect to this patient's medication regimen. The arrow in the figure represents the stylus/pointing device 56.

Figure 11:
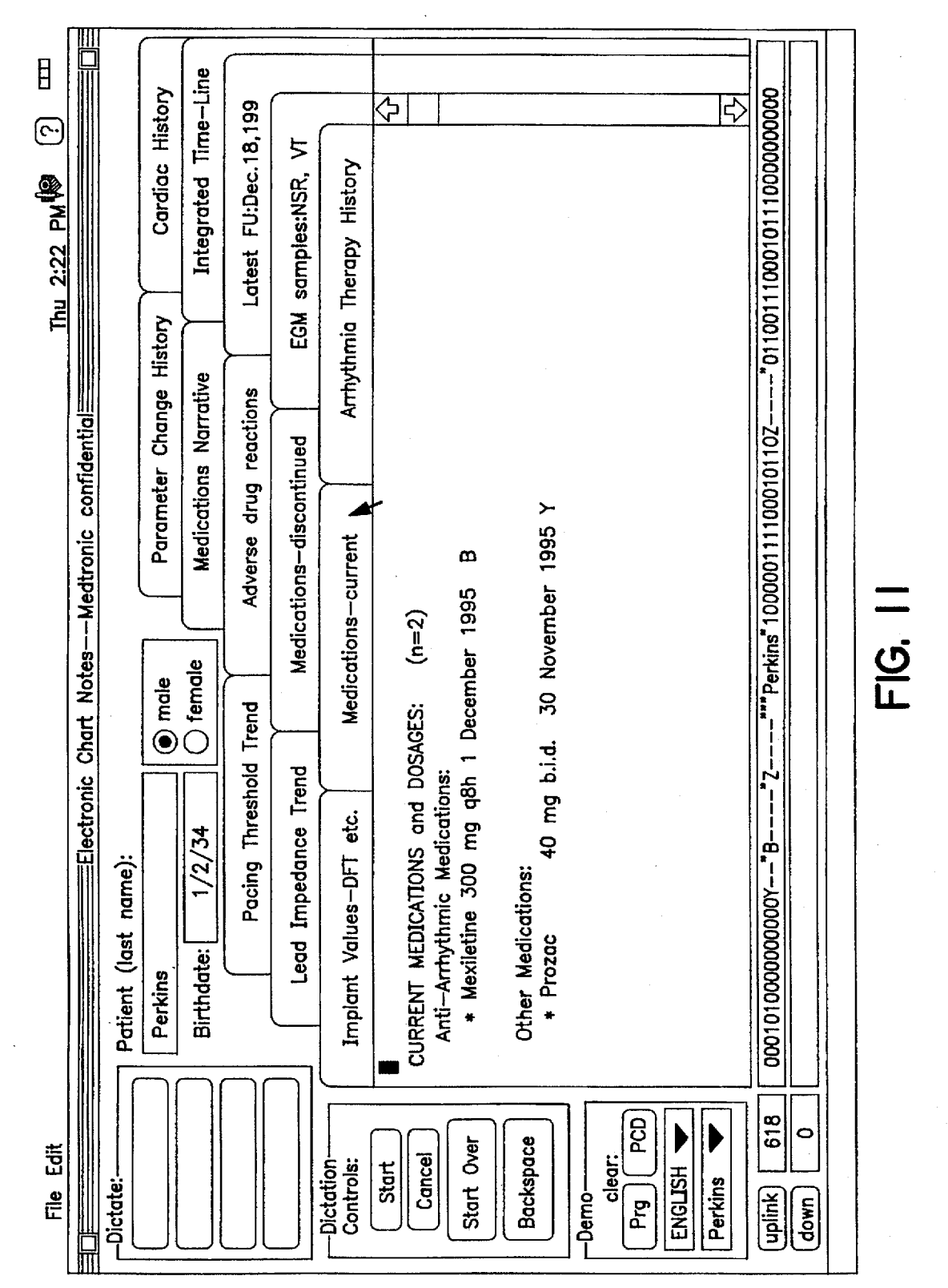

FIG. 11 shows the same information decoded from the patient related data bit string, including any further additions made by the physician, regarding the patient's medication regimen, in a tabular format report. The tabular format report is generated by conventional software means from the internal computer representation 104, which was itself derived from the patient related data bit string as recovered by uplink telemetry from the implanted medical device 10, and extended by further additions made by the physician. The extended patient related data bit string may be stored in the implanted medical device 10 by downlink telemetry, to store the updated information regarding the patient's history of medications.

The manner in which selected patient data from the patient related data bit string may be presented in tabular format is as follows. As the formal generative grammar is followed by software in the programmer, the physician's entries recorded in the patient related data bit string are used to select items from menus encountered during the use of the grammar, and also to enter values for variables (such as numbers and dates) encountered during the use. When a particular item in the generative grammar is followed, that item may optionally specify a side-effect to take place in the software, in particular, the recording of the value for the variable. For example, the use of a phase in the grammar stating that the physician has prescribed a certain drug for the patient at a particular dose on a particular date may not only cause the textual form of that phrase to be written, but also have the side-effect of generating an internal data record in the programmer's memory recording the drug, dosage, and starting date. From the internal data record, it is a simple matter to generate reports in tabular format by conventional software techniques.

Essential Components of the Method

The essential components of the method are as follows:

1) A generative grammar for the types of narratives about the patient which may be entered and stored.
2) A software algorithm capable of:
   a) constructing menus and data entry fields (i.e., variables) based on the generative grammar, and presenting them serially for physician input, where the next menu or data entry field to be presented depends upon both the prior entries and the generative grammar;
   b) constructing an internal computer representation of the patient related data;
   c) recording the physician's choices and data entries regarding the patient as a patient related data bit string for use in telemetry transmission to the implanted device;
   d) generating a textual narrative based on the physician's entries in conjunction with the generative grammar; and in the course of telemetry out of the bit string:
   e) decoding the patient related bit string formed from physician's choices and data entries, in conjunction with the generative grammar to generate the same textual narrative as originally generated; or
   e) alternatively, in conjunction with a correlated generative grammar for an alternative human language, to generate the textual narrative in that alternative human language.

A generative grammar of the invention is in a form that computer scientists call a "context-free grammar." (See Hopcroft, John E. and Ullman, Jeffrey D., *Introduction to Automata Theory, Languages, and Computation*, Addison-Wesley Publishing Company, 1979, page 79.) A grammar of this type is formally defined as $G=(V, T, P, S)$ where V is a finite set of variables (symbols); T is a finite set of terminals (text); P is a finite set of grammar rules of the form $A \rightarrow x$, where A is a variable and x is a string of items from the union of V and T; and S is a special variable called the start symbol, identifying the initial grammar rule to be followed when using the grammar.

In practical terms, the generative grammar G consists of a set of "re-write" rules indicating how the start symbol S may be successively replaced by substituting other variables V and text T for it, following the grammar rules. The ultimate result of the re-writing process is the replacement of all symbols V by text T; the resulting text T is the generated narrative. What the generated narrative says about the patient is determined by the choices and data entries made by the physician.

In further explanation, T is the set of terminals, each of which is text and is to be contrasted with V, the set of symbols, which are "nonterminals" in that they indicate the need for further replacement of the symbols with text in order to complete the generation of the text. In generating the text, software's job is to keep applying the generative grammar G until it has replaced all symbols with items requiring no further expansion or interpretation, i.e., the text or data entries, which are thus, "terminals." The S or "start symbol" S is the initial symbol which starts the process going. Replacing a symbol is done by finding the grammar rule in the generative grammar that has that symbol as its rule name, then putting the rule body in, in its place. The result may be that more symbols V have been inserted as a result of the inserted rule, so the process repeats. Eventually, no symbols V are left, and the result is the narrative text.

It may be noted that because the generative grammar G indicates what type of substitutions are required, but does not determine either the length or information content of the resulting text T, the physician may express as much or as little information about the patient as he or she chooses, within the domain of information covered by the generative grammar.

A portion of an English language generative grammar in the domain of medical histories for tachyarrhythmia patients is shown below. In this example, symbols V are written in angle brackets as: <symbol>; terminals (text T) appear within quotation marks "like this text" or as data entry fields in curly braces { } in which the physician enters text or numerical data, such as {patient name}. The start symbol, S, is <patient history >. The set of rules P consists of those items with a single <symbol> on the left hand side of an arrow --> and a list of <symbols> or "text" on the right hand side. In addition, the following notation is used on the right hand side of rules:

|= a vertical bar between items indicates a choice among alternatives.

*= an asterisk indicates that zero or more of the asterisked item or group of items may be used in the generation of the narrative.

+= a plus sign indicates that at least one, and perhaps more of the asterisked item or group of items may be used in the generation of the narrative.

( )= parentheses are used to group items to designated the scope of the |, *, or + signs.

| GENERATIVE GRAMMAR: | <patient history> |
|---|---|
| <patient history> -> | <introduction> ( <patient data> )* |
| <introduction> -> | <patient description> "with" |
| | <patient presentation> "." |
| <patient description> -> | {patient name} " is " ("a" | "an") |
| | {patient age in years} "year-old" ("male" | "female") |
| <patient presentation> -> | ( <previous event> | <dated event> | |
| | <diagnosis> ) |
| <previous event> -> | "a previous" <cardiac event> |
| <cardiac event> -> | ( <myocardial infarction> | "primary VF arrest" | |
| | "cardiac arrest" ) |
| <myocardial infarction> -> | (<infarct location description> | " " |
| | "myocardial infarction" |
| <infarct location description> -> | ( " " | "left" | "right") (" " | "inferior" | |
| | "superior") (" " | "anterior" | "posterior") |
| <dated event> -> | <cardiac event> "on" {a date} |
| <diagnosis> -> | (<arrhythmia>)$^+$(" " | <secondary to> ) |
| <arrhythmia> -> | ("primary VF" | "recurrent syncopal VT" | |
| | "syncopal VT" | "atrial fibrillation" | |
| | {other arrhythmia}) |
| <secondary to> -> | "secondary to" (<arrhythmia cause>)$^+$ |
| <arrhythmia cause> -> | (<underlying disease> | <cardiac event> ) |
| <underlying disease> -> | ("non-ischemic cardiomyopathy" | |
| | "coronary artery disease" | |
| | "primary electrical disease" | |
| | "ventricular dysplasia" | |
| | {other disease label}) |
| <patient data> -> | ( <medications> | <implant or surgery> | |
| | <cardiac assessment> ) |
| <medications> -> | . . . etc . . . |

Software Algorithm

The following is the algorithm for the above described software process, written in pseudocode form as is commonly understandable by persons practiced in the art. The numbers to the left of each line are line numbers for reference later in this description, and are not part of the algorithm:

```
(1)   BEGIN main
(2)       textualNarrative := nil;
(3)       currentRule := grammar rule whose name is the same as the start symbol
                        of the generative grammar;
(4)       currentTokenNumber := 0.
(5)       push currentRule and currentTokenNumber onto a stack;
(6)       processNextToken.
(7)   END;
(8)   BEGIN processNextToken
(9)       token := nil;
(10)      WHILE token is nil DO:
(11)          pop currentRule and currentTokenNumber off stack;
(12)          IF currentRule is nil THEN RETURN; /* exit here */
(13)              currentTokenNumber := currentTokenNumber + 1;
(14)          token := item in currentRule whose position is
                                    currentTokenNumber;
(15)      END_WHILE; /* found the next token to process */
(16)      push currentRule and currentTokenNumber onto stack;
(17)      IF token is a kind of rule THEN:
(18)          currentRule := token;
(19)          currentTokenNumber := 0;
(20)          push currentRule and currentTokenNumber onto stack;
(21)      ELSE /* token is not a kind of rule */
(22)          specification := retrieve from the generative grammar
                        the specifications for how this token is to be displayed
                        /* e.g., if the token is a "branch" point, the
                        specifications return a menu; if the token is text, the
                        specifications return an ASCII character string */
(23)          IF specification is not nil THEN
(24)              update graphic display using the specification;
(25)          IF specification requires user input THEN
                        /* a menu requires input, text does not */
(26)              value := get value for token from memory;
                        /* the internal computer representation 104 */
(27)              IF value is not nil THEN
(28)                  automatically enter the value for user
                        /* don't ask the user for a value he/she
```

```
                    has already entered earlier */
(29)            ELSE
(30)                get choice or value from physician [data entry case]
                    OR from the patient related data bit string
                    [retrieval case];
(31)                IF choice THEN
(32)                    currentRule := next rule specified
                            by physician's choice;
(33)                    currentTokenNumber := 0;
(34)                    push currentRule and currentToken
                            Number onto stack;
(35)                    add choice encoding to bit string;
(36)                ELSE /* value */
(37)                    store value as value for this token;
(38)                    add value encoding to bit string;
(39)                    append value to textualNarrative;
(40)                ENDIF /* choice or value */
(41)            ENDIF; /* value is nil */
(42)        ELSE /* specification does not require user input */
(43)            append text to the textualNarrative;
(44)        ENDIF; /* specification requires user input? */
(45)    ELSE /* specification is not nil */
(46)        CONTINUE;
(47)    ENDIF; /* specification is nil?*/
(48)  ENDIF; /* token is kind of rule?*/
(49)  processNextToken; /* recursive call */
(50) END.
```

The software of the invention performs the above algorithm in the process of generating, encoding and downlink telemetering patient related data as a bit string to the implanted medical device. It also re-performs the identical algorithm, using the uplink telemetered patient related data bit string in lieu of physician input, to decode and regenerate the textual narrative or other tabular information from the patient related bit string.

The method of the invention involves automatically starting the process of constructing a narrative by initializing the process with the grammar's start symbol S, finding the rule in the grammar G that has the start symbol S on the rule's the left-hand side (algorithm step 3). The right-hand side of the corresponding rule is interpreted as a procedure, as follows. The items on the right-hand side are processed sequentially, from left-to-right, as controlled by the incrementing of the currentTokenNumber variable (algorithm step 13) until the end of the rule is reached (algorithm step 14). When a symbol V is encountered, the software finds the rule, if any, in the grammar G that has that symbol V on the left-hand side (step 17), and proceeds to interpret the right-hand side of that rule using this same procedure (step 49). If, instead, terminal text T is encountered (step 21 and 42), that text is inserted into the narrative report displayed to the physician (step 43), but not into the bit string which is encoding the physician's choices and data entries. When a group of items involving a choice among alternatives is encountered, a menu is constructed from those alternatives and displayed to the physician (step 24). The menu choice entered by the physician using the stylus pointing device 56 or keyboard 65 determines the item which the software will process next (step 32), and also is encoded as a binary number whose bits are added (step 35) to the end of the (initially empty) bit string encoding the physician's entries. A group of items in a rule of the generative grammar which are "starred," as in (<patient data>)*, results in the program repeating the processing of the item(s) unless and until the physician elects (via an automatically generated menu which is produced by the software after each processing of the item) to stop the processing of that group. A group of items which have a + designation result in the program processing the items at least once, before the physician is given the option of repeating the group or proceeding. Finally, an item which requires physician input into a data entry field (e.g., {patient name} or {patient age in years}) is processed by the software to produce an appropriately labeled data entry field (step 24) for user input (step 30).

Menus and Data Entry Fields

The specific appearance of the menus, data entry fields, and narrative text as they are generated are dependent upon the Computer operating system used to implement the inventive method and is not part of the invention per se. As shown with reference to FIGS. 4, 6, and 10, whatever the computer operating system, it displays the textual narrative as it is generated and selected by the physician on the programmer display 55 in the fashion that it will be reproduced on subsequent interrogation.

Constructing an Internal Computer Representation

A significant aspect of the invention is the use of the software to build an internal computer representation 104 of the patient's medical status and/or medical history as a side-effect of the generation of the narrative as shown in algorithm step 37. This internal computer representation 104 is used wherever possible to supply values for further items encountered in the narrative (step 26) rather than asking for redundant input from the user (step 28 vs step 30). In this manner, the previously interpreted portion of the patient related data bit string can alter the manner in which the algorithm processes the remainder of the patient related data bit string, without need for input by the user.

Furthermore, by way of example, whenever the physician constructs a portion of the narrative mentioning a <cardiac event> (possibly giving a date associated with that event), an internal computer representation that the patient had the event happen to him or her is also constructed. Similarly, whenever the physician mentions in the narrative that the patient has undergone a particular medical procedure (possibly giving the date), that fact is also represented internally as well. Subsequently, the menus and data entry fields determined by the grammar may be expanded or altered based on this internal representation. For example, once the physician has mentioned that the patient has experienced a particular cardiac event, that event becomes a possible candidate for the underlying cause of other medical problems to be discussed in the narrative, and is incorporated into the menu presented to the physician when an <underlying cause> is called for. Similarly, any specific date entered by the physician earlier in the narrative becomes a candidate for inclusion on menus of dates at various later points in the narrative. This aspect of the invention allows for more efficient entry of information by the physician, and more natural sounding narratives.

Constructing the Patient Related Data Bit String

Initially, at the start of authoring a narrative, the bit string encoding the narrative is empty. As the physician makes menu choices and data entries, he/she is guided by software generated prompts and menu choices (step 24) appearing on the display 55. As it undergoes its processing of the grammar rules, the software algorithm also records the menu choice selections and data entries the physician makes as binary numbers, which are appended to the bit string (step 35). With respect to menu choice selections, the binary numbers simply encode the ordinal position of the menu choice selected by the physician. Thus, for example, five bits are sufficient to encode the physician's selection from among as many as 32 different menu choices presented for a variable. Such a selection of one menu choice from among three choices is presented in screen display 67 of FIG. 4.

Similarly, as the physician enters the patient name and other patient related data in alphanumeric form or as dates, these data are encoded into ASCII code binary form and appended to the bit string (step 38). The terminal text T items in the grammar are specifically not encoded and included in the bit string (note absence of additions to bit string at step 43). Rather, these remain implicit in the encoding of the narrative, by virtue of the fact that the identity of the generative grammar which produced the bit string encoding is known and recorded with the bit string.

The encoding of the patient related data bit string is entirely complete at the same time as the physician completes the narrative with his/her last entry. All that remains is to give the physician the option of cancelling the whole entry, or accepting it. Then, the bit string is ready for downlinking whenever the physician puts the telemetry head 22 over the patient's device 10.

As shown in FIG. 4, the encoded bit string is telemetered to the implanted medical device 10 employing the downlink telemetry capabilities of the external programmer 20 upon completion of the bit string as described above. At this point in the explanation of the system, it is assumed that the telemetered encoded bit string identifying the grammar and representing the patient data is received and stored in the memory of the implanted device 10 and such storage is confirmed back to the programmer 20 using the pre-existing program confirmation functions.

When storing the patient related data bit string in the patient's implanted device 10, the bit string is encoded with an identification of the version of the generative grammar that was used, e.g. version 2.1. It is stored in memory addresses of RAM 30 that are not to be written over during internal device routines. With the exception of designating a memory block in RAM 30 that cannot be written over by the internally generated diagnostic and therapy recording data functions of the implanted medical device 20, no other change in the implanted device 10 is necessary to implement the system of the present invention. In some instances, pre-existing implanted medical devices 10 have RAM memory bytes that are reserved for unspecified future uses, as shown, for example, in the above-incorporated '513 patent. All that is necessary is to use those byte addresses for the bit string to be recorded.

Generating Narrative Text

In contrast to the encoding of the bit string, the textual form of the narrative being produced by the generative grammar includes the values for variables entered by the physician (step 39), and all terminal text items in the grammar (step 43). These are preferably displayed to the physician as the narrative is constructed, such that the physician has the experience of the software "taking dictation" of the patient's medical record as the physician enters it (refer to FIGS. 6 and 10). The completed narrative may also be stored in memory for future use and/or printed out and/or stored on a floppy disk.

In FIG. 6, the display screen 55 displays the textual narrative as it is being interactively formulated from the text of the grammar augmented by the selections of menu choices and data field entries made by the physician using the stylus/pointing device 56 or the keyboard 65. An example of this is also shown in the text display 64 of FIG. 4 in relation to the next menu choice 67 also displayed to the physician for selection using the stylus/pointing device 56.

Decoding the Bit String into the Same or an Alternative Human Language

During uplink interrogation of implanted medical device 10 by the programmer 20, the grammar identification and version number, and the patient related data bit string from which the textual narrative is to be regenerated are telemetered out as also shown in FIG. 5. In response, the programmer 20 software retrieves the appropriate generative grammar from disk drive 52. The software then decodes the telemetered bit string by applying the retrieved generative grammar to the bit string. Processing of the generative grammar proceeds as described above, using the identical algorithm, with the exception that entries for menu choices and data values are read from the uplinked patient related data bit string rather than from prompts to the physician.

The internal computer representation 104 of the patient is generated (in step 37) while the patient related data bit suing is being used as input to the generative grammar, as a result of the side-effects of the following the grammar. The generation of menus (which need not be displayed), the generation of text from the generative grammar, the generation of the internal computer representation 104 and the decoding of the retrieved patient related data bit string all occur simultaneously, as the generative grammar is followed, using the patient related data bit string as the source of choices and values, rather than the physician. The simultaneous generation of the internal computer representation 104 is an essential aspect of the invention, because it permits the menu choices called for by the grammar G to contain the same list of possibilities that the original, entering physician was presented with upon reaching the corresponding point in the narrative. Thus, the next binary number in the bit string at that point can be correctly interpreted as the appropriate menu choice from the correct menu and corresponding to the authoring physician's selection.

Summary

The system of the present invention significantly decreases the amount of memory consumed in the implanted medical device 10 without placing rigid constraints upon the length of the narrative or the permissible characters used and without requiring potentially frustrating planning by the person entering the data to fit their narrative into a prescribed space. Because the narrative summaries of patient histories, implant procedures, catheterization findings, follow-up visits, etc., tend to be highly stylized in their wording and content, it is possible to write restricted grammars of English (and presumably, other natural human languages) that cover the universe of possible narratives within a constrained domain of discourse.

As illustrated in FIGS. 6 and 10, given a grammar for the narrative domain, the physician may enter a specific narrative by choosing from alternatives for the next successive phase of their narrative from a menu dynamically constructed using the generative grammar resident in the programmer. That is, the programmer, following the generative grammar rules, starts the narrative using a standard beginning. The user then selects the next phrase to be written from a menu presented on the programmer display. The corresponding phrase is added to the end of the growing narrative, and the next menu choice is presented. What menu appears next depends upon the prior entry, and the rules in the generative grammar. Likewise, at appropriate points in the narrative, the user may be prompted for numerical or string values of variables to "fill in a blank" in a phrase, i.e., to complete a data entry field. The length of the overall narrative is open-ended, with the user completing the narrative by making the appropriate menu choice at an grammatically appropriate point. The result is a narrative created, and therefore re-constructable, from a series of menu choices and scalar values entered by the user in conjunction with the playback of a set of grammar rules stored on the programmer.

Since the grammar rules and the resulting text string can reside in the programmer, all that needs to be stored and retrieved from the implanted medical device is an encoding of the menu choices, the scalar values, and the identity of the generative grammar that may be used to re-generate the narrative from this information. Because most of the menus are short, involving a selection from only a handful of options, each menu choice by the user can usually be encoded in a few bits of data. Numerical values and strings, of course, require 8 bits for integers and individual characters.

In a prototype implementation of a grammar for patient histories, it has been found that narrative histories (typically 2,000–4,000 characters in length) can be stored using a few hundred bits (less if the patient and physician's names are short). Longer narratives require proportionally less memory, since the length of the narrative is usually due to more phases from menu choices, rather than more values entered as integers or strings. It is therefore feasible to assume that a narrative summary of 4–6 sentences or more in length may be stored in about 1 Kb of RAM. Thus, narrative summaries for each of the following could be stored in about 10–12 Kb of dedicated RAM:

Patient's cardiac medical history
Anti-arrhythmic drug therapy
Physical exam findings
ECG interpretations
Echocardiogram Findings
Cardiac Catheterization Findings
Hospital discharge summary
Implant procedure summary
Summary of the 3 most recent follow-up visits To use this technique, a generative grammar must be written for each of the above domains and any other narrative summary, and that generative grammar must be tested with physicians to verify that it has been expanded sufficiently to cover the vast majority of types of information they might wish to express under that category. Development of a generative grammar is a collaborative, iterative process, made more convenient by the fact that the human interface for entering and re-constructing narratives can be automatically generated from a text file of the grammar rules themselves.

The ability to re-generate stored narratives in other hurt Jan languages than the one used for data entry is possible using suitably constructed generative grammars. Thus, a patient's medical history and other narrative information can be retrieved in the native language of the physician at any location on the globe to which the patient might travel, given a suitably equipped programmer. This is a feature of the technique which would not be obviated simply by increasing memory capacity and telemetry transmission rate.

In addition, the system and method is not limited to textual narratives, and patient related dam that is stored in textual narrative form may be regenerated and may be presented in a number of formats other than the textual narrative. Based on the selections of menu choices and the dam entries made in the free-form data entry fields, several separate tabular reports may be regenerated, e.g., a listing of past and present medications, a chronological history of past medications, adverse drug reactions, chronological implant history, etc.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired.

While there have been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

I claim:

1. In a system for storing patient related data within an implanted medical device implanted in an ambulatory patient and for regenerating the patient related information with an external programmer of the type comprising a medical device telemetry transceiver in the implanted medical device operable in a downlink telemetry mode for receiving patient related data bit strings and operable in an uplink telemetry mode for transmitting patient related data bit strings and memory locations in the implanted medical device for storing patient related data bit strings transmitted in downlink telemetry to the implanted medical device telemetry transceiver, a method of composing and storing textual narrative patient related data in such memory locations employing such an external programmer capable of initiating said uplink and downlink telemetry comprising the steps of:

storing a generative grammar defining a finite set of variables, and a set of grammar rules from which a textual narrative of patient related data can be generated by appropriate selections of choices from menus and values of variables;

encoding selections of choices from menus and values from variables as a patient related data bit string; and operating said programmer telemetry transceiver in said downlink telemetry mode for signaling said implanted medical device telemetry transceiver to operate in said downlink telemetry mode and for transmitting said patient related data bit strings to said implanted medical device telemetry transceiver for receipt and storage in said implanted medical device memory locations.

2. The method of claim 1 further comprising the step of:
recording an identification code of the generative grammar with the patient related data bit string.

3. The method of claim 2 further comprising the steps of:
operating said programmer telemetry transceiver in said uplink telemetry mode for signalling said implanted medical device telemetry transceiver to operate in said uplink telemetry mode and for transmitting said patient related data bit strings to said programmer telemetry transceiver for receipt thereby; and identifying said generative grammar from said identification code; and regenerating said textual narrative patient related data from the identified generative grammar and the patient related data bit string.

4. The method of claim 3 further comprising the step of:
regenerating selected patient data in tabular format from said patient related data bit string.

5. The method of claim 3 wherein said regenerating step further comprises:
regenerating said textual narrative patient related data from the patient related data bit string in any selected human language for which there exists a formal generative grammar that is correlated to the original formal generative grammar used to enter and store the patient related data.

6. The method of claim 1 further comprising the steps of:
operating said programmer telemetry transceiver in said uplink telemetry mode for signaling said implanted medical device telemetry transceiver to operate in said uplink telemetry mode and for transmitting said patient related data bit strings to said programmer telemetry transceiver for receipt thereby; and regenerating said textual narrative patient related data from the identified generative grammar and the patient related data bit string.

7. The method of claim 6 further comprising the step of:
regenerating selected patient data in tabular format from said patient related data bit string.

8. The method of claim 6 wherein said regenerating step further comprises:
regenerating said textual narrative patient related data from the patient related data bit string in any selected human language for which there exists a formal generative grammar that is correlated to the original formal generative grammar used to enter and store the patient related data.

9. A system for storing patient related data within an implanted medical device implanted in an ambulatory patient and for regenerating the patient related information with an external programmer comprising:

in the implanted medical device:
an implanted medical device telemetry transceiver operable in a downlink telemetry mode for receiving patient related data bit strings and operable in an uplink telemetry mode for transmitting patient related data bit strings; and memory locations for storing patient related data bit strings transmitted in downlink telemetry to said implanted medical device telemetry transceiver; and in the external programmer:
means for storing a generative grammar defining a finite set of variables, and a set of grammar rules from which a textual narrative of patient related data can be generated by appropriate selections of variables in an external programmer memory;

means for encoding selections of patient related variables as a patient related data bit string; and means for operating said programmer telemetry transceiver in said downlink telemetry mode for signalling said implanted medical device telemetry transceiver to operate in said downlink telemetry mode and for transmitting said patient related data bit strings to said implanted medical device telemetry transceiver for receipt and storage in said implanted medical device memory locations.

10. The system of claim 9 further comprising:
means for recording an identification code of the grammar with the patient related data bit string.

11. The system of claim 10 further comprising:
means for operating said programmer telemetry transceiver in said uplink telemetry mode for signaling said implanted medical device telemetry transceiver to operate in said uplink telemetry mode and for transmitting said patient related data bit strings to said programmer telemetry transceiver for receipt thereby;

means for identifying said generative grammar from said identification code; and means for regenerating said textual narrative patient related data from the identified generative grammar and the patient related data bit string.

12. The system of claim 11 further comprising:
means for regenerating selected patient data in tabular format from said patient related data bit string.

13. The system of claim 11 wherein said regenerating means further comprises:
means for regenerating said textual narrative patient related data from the patient related data bit string in any selected human language for which there exists a formal generative grammar that is correlated to the original formal generative grammar used to enter and store the patient related data.

14. The system of claim 9 further comprising:
means for operating said programmer telemetry transceiver in said uplink telemetry mode for signalling said implanted medical device telemetry transceiver to operate in said uplink telemetry mode and for transmitting said patient related data bit strings to said programmer telemetry transceiver for receipt thereby; and means for regenerating said textual narrative patient related data from the identified generative grammar and the patient related data bit string.

15. The system of claim 14 further comprising:
means for regenerating selected patient data in tabular format from said patient related data bit string.

16. The system of claim 14 wherein said regenerating means further comprises:
means for regenerating said textual narrative patient related data from the patient related data bit suing in any selected human language for which there exists a formal generative grammar that is correlated to the original formal generative grammar used to enter and store the patient related data.

17. A system for storing patient related data within an implanted medical device implanted in an ambulatory patient and for regenerating the patient related information with an external programmer comprising:

in the implanted medical device:
an implanted medical device telemetry transceiver operable in a downlink telemetry mode for receiving patient related data bit strings and operable in an uplink telemetry mode for transmitting patient related data bit strings; and memory locations for storing patient related data bit strings transmitted in downlink telemetry to said implanted medical device telemetry transceiver; and in the external programmer:

programmer memory for storing a generative grammar defining a finite set of variables, including menu choices and data entry fields, and a set of grammar rules from which a textual narrative of patient related data can be generated by appropriate selections of menu choices and data entries;

means for applying said stored generative grammar and initiating the generation of a narrative of patient related data;

display means for successively displaying the menu choices and data entry fields for selection and entry by the user in compliance with the generative grammar rules and in dependence on the selections made by the user;

means for entering the selection of menu choices and data entries; means for encoding the selections of menu choices and the data entries as a patient related bit string; and a programmer telemetry transceiver operable in said downlink telemetry mode for signaling said implanted medical device telemetry transceiver to operate in said downlink telemetry mode and for transmitting said patient related data bit strings to said implanted medical device telemetry transceiver for receipt and storage in said implanted medical device memory locations.

18. The system of claim 17 wherein said external programmer further comprises:

means for constructing internal computer records of the patient related data as the selections and entries are made by the user.

19. The system of claim 18 wherein said external programmer further comprises:

means for operating said external programmer telemetry transceiver in said uplink telemetry mode for signaling said implanted medical device telemetry transceiver to retrieve and transmit stored patient related data bit strings in said uplink telemetry mode and for receiving transmitted patient related data bit strings; and means for regenerating the textual narrative from the received patient related data bit string employing the internal computer records in conjunction with the generative grammar to make appropriate selections of menu choices and data entries using information retrieved from the internal computer records.

20. The system of claim 17 wherein said external programmer further comprises:

means for operating said external programmer telemetry transceiver in said uplink telemetry mode for signalling said implanted medical device telemetry transceiver to retrieve and transmit stored patient related data bit strings in said uplink telemetry mode and for receiving transmitted patient related data bit strings; and means for regenerating the textual narrative from the received patient related data bit suing employing the internal computer records in conjunction with the generative grammar to make appropriate selections of menu choices and data entries using information retrieved from the internal computer records.

21. A method for storing patient related textual narrative within an implanted medical device and for regenerating the patient related textual narrative with an external programmer, employing:

an implanted medical device comprising a telemetry transceiver operable in a downlink telemetry mode for receiving patient related data bit strings and operable in an uplink telemetry mode for transmitting patient related data bit strings and memory for storing patient related data bit strings transmitted in downlink telemetry to the implanted medical device telemetry transceiver; and a programmer comprising a telemetry transceiver operable in said downlink telemetry mode and in said uplink telemetry mode, a memory, a display means for displaying menu choices, an input means for accepting selections of menu choices and data entries and a processor means for encoding menu selections as patient related bit strings;

the method comprising the steps of:

storing a generative grammar defining a finite set of variables, including menu choices and data entry fields, and a set of grammar rules from which a textual narrative of patient related data can be generated by appropriate selections of menu choices and data entries in the programmer memory;

initiating the generation of a narrative of patient related data;

successively displaying the menu choices and data entry fields for selection and entry by the user in compliance with the generative grammar rules and in dependence on the selections made by the user;

accepting the selection of menu choices and data entries made by a user;

encoding the selections of menu choices and the data entries as a patient related bit string; and operating the programmer telemetry transceiver in said downlink telemetry mode for signaling said implanted medical device telemetry transceiver to operate in said downlink telemetry mode and for transmitting said patient related data bit strings to said implanted medical device telemetry transceiver for receipt and storage in said implanted medical device memory locations.

22. The method of claim 21 further comprising the step of:

constructing internal computer records in the programmer memory of the patient related data as the selections and entries are made by the user.

23. The method claim 22 further comprising the steps of:

operating the programmer telemetry transceiver in said uplink telemetry mode to signal the implanted medical device telemetry transceiver to retrieve and transmit stored patient related data bit strings in said uplink telemetry mode and to receive transmitted patient related data bit strings; and operating the programmer processor to regenerate the textual narrative from the received patient related data bit string by employing the internal computer records in conjunction with the generative grammar.

24. The method of claim 21 further comprising the steps of:

operating the programmer telemetry transceiver in said uplink telemetry mode to signal the implanted medical device telemetry transceiver to retrieve and transmit stored patient related data bit strings in said uplink telemetry mode and to receive transmitted patient related data bit strings; and operating the programmer processor to regenerate the textual narrative from the received patient related data bit string by employing the generative grammar.

* * * * *